United States Patent [19]

Troiani et al.

[11] 4,426,393

[45] Jan. 17, 1984

[54] METHOD OF PROTECTING USEFUL PLANTS AND FORMULATIONS FOR USE IN SAID METHOD

[75] Inventors: Nicola Troiani, Milan; Franco Gozzo, S. Donato Milanese; Simone Lorusso, San Giuliano Milanese, all of Italy

[73] Assignee: Montedison S.p.A., Milan, Italy

[21] Appl. No.: 306,730

[22] Filed: Sep. 29, 1981

Related U.S. Application Data

[62] Division of Ser. No. 98,027, Nov. 28, 1979, abandoned.

[30] Foreign Application Priority Data

Nov. 29, 1978 [IT] Italy ............................... 30322 A/78

[51] Int. Cl.$^3$ ............................................. A01N 33/26
[52] U.S. Cl. .................................... 424/327; 564/226; 564/229

[58] Field of Search ......................................... 424/327

[56] References Cited

U.S. PATENT DOCUMENTS 2,947,782 8/1960 Benneville et al. ................. 260/551
3,234,255 2/1966 Hackmann et al. ................. 260/454

OTHER PUBLICATIONS

Bamberger et al., Berichte, vol. 35, pp. 1082–1093, 1902.

*Primary Examiner*—Allen J. Robinson

[57] ABSTRACT

There are disclosed arylhydrazo-aldoximes which, as such, as tautomers, and in the form of organic or inorganic salts thereof, are active in preventing and treating infections of useful plants by fungi, and in immunizing plants against such infections.

7 Claims, No Drawings

METHOD OF PROTECTING USEFUL PLANTS AND FORMULATIONS FOR USE IN SAID METHOD

This is a Rule 60 Division of our application Ser. No. 98,027 filed Nov. 28, 1979, and now abandoned.

THE PRIOR ART

Some arylhydrazo-aldoximes are known from the publications of E. Bemberger et al (see Berichte 35, 1902, pp. 72-74; ibid p. 1085; and ibid 36, 1903, p. 57). However, no use for such arylhydrazo-aldoximes is known except only as intermediates for obtaining other compounds.

THE PRESENT INVENTION

One object of this invention is to show the biological activity of the arylhydrazo-aldoximes.

Another object is to provide a method of using arylhydrazo-aldoximes to fight infection of useful plants by fungi.

A further object is to provide new fungicidally active arylhydrazo-aldoximes.

These and other objects are achieved by the present invention based on the discovery that arylhydrazo-aldoximes having the general formula:

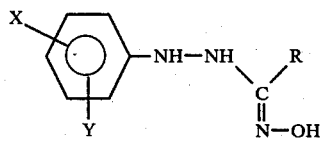

or their tautomers:

in which

X and Y=H, halogen, $C_1$-$C_5$ alkyl, halogenated alkyl, alkoxyl or $NO_2$; and R=H, $C_1$-$C_5$ alkyl, phenyl or subsubstituted phenyl, are active as such, or in the form of their organic or inorganic salts, and in doses of as low as 0.01%, in preventing (hindering) the infection of plants by fungi; in treating plants which have been infected; and in immunizing plants against infection by inhibiting spreading of the infection even if applied at a distance from the site of the infecting fungi.

The following Table I lists specific arylhydrazoaldoximes which we have tested and found to be fungicidally active, including arylhydrazo-aldoximes which are new products in the art as well as arylhydrazo-aldoximes known in the literature for which bibliographic data is provided in the Table. The arylhydrazo-aldoximes are prepared by methods based on the literature cited.

The arylhydrazo-aldoximes according to the present invention can be applied to the plant as such or in the form of formulates prepared by conventional techniques: they can be mixed with inert powders, such as, e.g., kieselguhr, activated carbon, gypsum, urea, etc., or they can be made to absorb, having recourse, if necessary, to surfactants, in order to obtain wettable powders; they can be also dissolved, or dispersed, or emulsified in water, or applied as solutions in organic solvents.

TABLE 1
PROPERTIES OF THE COMPOUNDS OF GENERAL FORMULA 1

| Item | X | Y | R | FORM (Free Base of Salt) | M.P. °C. | C Calc. % | C Found % | H Calc. % | H Found % | N Calc. % | N Found % |
|---|---|---|---|---|---|---|---|---|---|---|---|
| M 9933 | 4-Cl | H | H | hydrochloride | 118 | 37.87 | 37.60 | 4.00 | 4.01 | 18.93 | 19.00 |
| 9340 | 2-Me | H | $CH_3$ | | 116 | 60.31 | 59.68 | 7.31 | 7.32 | 23.44 | 23.49 |
| 9341 | 2-Me | H | $CH_3$ | hydrochloride | 180 | 50.12 | 49.82 | 6.65 | 6.54 | 19.48 | 19.31 |
| 6980 | 4-Me | H | $CH_3$ | hydrochloride | 148 | 50.12 | 49.96 | 6.65 | 6.56 | 19.48 | 19.49 |
| 7048 | 2-Cl | H | $CH_3$ | | 128 | 48.13 | 47.89 | 5.05 | 4.80 | 21.05 | 20.85 |
| 7049 | 2-Cl | H | $CH_3$ | hydrochloride | 185 | 40.70 | 40.63 | 4.70 | 4.62 | 17.80 | 17.46 |
| 7005 | 3-Cl | H | $CH_3$ | | 148 | 48.13 | 48.00 | 5.05 | 5.04 | 21.05 | 21.25 |
| 7006 | 3-Cl | H | $CH_3$ | hydrochloride | 160 | 40.70 | 40.44 | 4.70 | 4.60 | 17.80 | 17.83 |
| 10027 | 2-F | H | $CH_3$ | | 140 | 52.45 | 52.35 | 5.50 | 5.61 | 22.42 | 22.29 |
| 10028 | 2-F | H | $CH_3$ | hydrochloride | 180 | 43.74 | 43.66 | 5.05 | 5.10 | 19.14 | 19.22 |
| 7046 | 3-$CF_3$ | H | $CH_3$ | | 115 | 46.35 | 46.05 | 4.32 | 4.24 | 18.02 | 18.10 |
| 7047 | 3-$CF_3$ | H | $CH_3$ | hydrochloride | 161 | 40.08 | 40.18 | 4.11 | 4.06 | 15.58 | 15.40 |
| 6879 | 4-OMe | H | $CH_3$ | | 105 | 55.37 | 55.04 | 6.71 | 6.73 | 21.52 | 21.38 |
| 9390 | 3-Me | 5-Me | $CH_3$ | | 124 | 62.15 | 62.45 | 7.82 | 7.86 | 21.14 | 21.18 |
| 9391 | 3-Me | 5-Me | $CH_3$ | hydrochloride | 170 | 52.29 | 52.37 | 7.02 | 6.89 | 18.29 | 18.15 |
| 7009 | 3-Cl | 4-Cl | $CH_3$ | | 150 | 41.05 | 41.09 | 3.87 | 3.90 | 17.95 | 18.24 |
| 7010 | 3-Cl | 4-Cl | $CH_3$ | hydrochloride | 156 | 35.52 | 35.47 | 3.72 | 3.67 | 15.53 | 15.43 |
| 9284 | 3-Cl | 4-Cl | $CH_3$ | oxalate | 160 | 38.70 | 39.00 | 3.60 | 3.70 | 15.0 | 15.0 |
| 9288 | 3-Cl | 4-Cl | $CH_3$ | p-toluene sulphonate | 182 | 44.30 | 45.10 | 4.20 | 4.40 | 10.30 | 10.50 |
| 9333 | 3-Cl | 5-Cl | $CH_3$ | | 155 | 41.05 | 41.19 | 3.89 | 3.83 | 17.95 | 17.96 |
| 9335 | 3-Cl | 5-Cl | $CH_3$ | hydrochloride | 114 | 35.52 | 35.56 | 3.72 | 3.60 | 15.53 | 15.44 |
| 9373 | 2-Me | H | $C_2H_5$ | | 103 | 62.15 | 62.56 | 7.82 | 8.06 | 21.74 | 21.97 |
| 9374 | 2-Me | H | $C_2H_5$ | hydrochloride | 159 | 52.59 | 51.86 | 7.02 | 6.95 | 18.29 | 18.18 |
| 7045 | 4-Me | H | $C_2H_5$ | hydrochloride | 145 | 52.59 | 51.94 | 7.02 | 6.95 | 18.29 | 18.07 |
| 7087 | 2-Cl | H | $C_2H_5$ | | 111 | 50.59 | 5.66 | 5.68 | 19.67 | 19.71 | |
| 7088 | 2-Cl | H | $C_2H_5$ | hydrochloride | 160 | 43.22 | 43.06 | 5.24 | 5.50 | 16.80 | 16.09 |
| 6984 | 3-Cl | H | $C_2H_5$ | | 112 | 50.59 | 50.68 | 5.66 | 5.75 | 19.67 | 20.43 |
| 6985 | 3-Cl | H | $C_2H_5$ | hydrochloride | 148 | 43.22 | 43.03 | 5.24 | 5.23 | 16.80 | 16.97 |
| 6981 | 4-Cl | H | $C_2H_5$ | hydrochloride | 166 | 43.22 | 43.23 | 5.24 | 5.27 | 16.80 | 16.75 |
| 7090 | 3-$CF_3$ | H | $C_2H_5$ | | 106 | 48.58 | 4.89 | 4.73 | 17.00 | 16.93 | |

TABLE 1-continued
PROPERTIES OF THE COMPOUNDS OF GENERAL FORMULA 1

| Item | X | Y | R | FORM (Free Base of Salt) | M.P. °C. | C Calc. % | C Found % | H Calc. % | H Found % | N Calc. % | N Found % |
|---|---|---|---|---|---|---|---|---|---|---|---|
| 7091 | 3-CF$_3$ | H | C$_2$H$_5$ | hydrochloride | 155 | 42.34 | 42.53 | 4.62 | 4.57 | 14.81 | 14.86 |
| 9396 | 3-Me | 5-Me | C$_2$H$_5$ | hydrochloride | 150 | 54.21 | 54.37 | 7.44 | 7.45 | 17.24 | 17.05 |
| 9466 | 2-Me | 6-Me | C$_2$H$_5$ | | 94 | 63.74 | 63.64 | 8.27 | 8.48 | 20.27 | 20.44 |
| 9467 | 2-Me | 6-Me | C$_2$H$_5$ | hydrochloride | 145 | 54.21 | 53.51 | 7.44 | 7.50 | 17.24 | 17.02 |
| 6948 | 2-Me | 4-Cl | C$_2$H$_5$ | | 112 | 52.75 | 51.75 | 6.20 | 6.04 | 18.45 | 18.01 |
| 6951 | 2-Me | 4-Cl | C$_2$H$_5$ | hydrochloride | 175 | 45.47 | 45.36 | 5.72 | 5.81 | 15.91 | 15.66 |
| 6882 | 2-Cl | 4-Cl | C$_2$H$_5$ | | 130 | 45.58 | 45.31 | 4.47 | 4.42 | 16.94 | 16.65 |
| 6982 | 2-Cl | 4-Cl | C$_2$H$_5$ | hydrochloride | 182 | 38.00 | 37.91 | 4.25 | 4.26 | 14.76 | 14.62 |
| 6950 | 3-Cl | 4-Cl | C$_2$H$_5$ | | 125 | 43.57 | 43.06 | 4.47 | 4.40 | 10.93 | 17.11 |
| 6953 | 3-Cl | 4-Cl | C$_2$H$_5$ | hydrochloride | 152 | 38.00 | 38.05 | 4.25 | 4.37 | 14.76 | 14.50 |
| 9289 | 3-Cl | 4-Cl | C$_2$H$_5$ | oxalate | 147 | 39.70 | 39.59 | 3.87 | 3.96 | 12.43 | 12.25 |
| 9290 | 3-Cl | 4-Cl | C$_2$H$_5$ | p-toluene sulphonate | 166 | 45.72 | 45.55 | 4.56 | 4.66 | 10.00 | 9.67 |
| 9363 | 3-Cl | 5-Cl | C$_2$H$_5$ | | 127 | 43.57 | 43.35 | 4.47 | 4.41 | 16.93 | 16.85 |
| 9371 | 3-Cl | 5-Cl | C$_2$H$_5$ | hydrochloride | 160 | 38.00 | 37.94 | 4.25 | 4.23 | 14.76 | 14.56 |
| 7493 | H | H | C$_6$H$_4$(4-Cl) | hydrochloride | 148 | 52.37 | 53.13 | 4.39 | 4.84 | 14.09 | 14.07 |
| 6881 | 4-Cl | H | C$_2$H$_5$ | | 98 | 50.59 | 49.65 | 5.66 | 5.60 | 19.67 | 19.36 |
| 7496 | H | H | C$_6$H$_3$(3,4-Cl$_2$) | hydrochloride | 158 | 46.94 | 46.56 | 3.63 | 3.59 | 12.63 | 12.54 |
| 6424 | H | H | CH$_3$ | | Bamberger, Frei, Berichte 35, 1088 | | | | | | |
| 6425 | 4-Me | H | CH$_3$ | | Bamberger, Berichte 35, 756 | | | | | | |
| 7007 | 4-Cl | H | CH$_3$ | | Bamberger, Berichte 35, 59 | | | | | | |
| 7008 | 4-Cl | H | CH$_3$ | hydrochloride | Bamberger, Berichte 35, 59 | | | | | | |
| 7043 | 2-Cl | 4-Cl | CH$_3$ | | Bamberger, Berichte 35, 61 | | | | | | |
| 7044 | 2-Cl | 4-Cl | CH$_3$ | hydrochloride | Bamberger, Berichte 35, 61 | | | | | | |
| 6954 | H | H | C$_2$H$_5$ | | Bamberger, Frei Berichte 35, 1092 | | | | | | |
| 7495 | H | H | C$_6$H$_5$ | hydrochloride | Bamberger, Frei, Berichte 35, 1091 | | | | | | |

The activity has been tested on various species of plants artifically infected with noxious fungi before (to determine the curative activity) and after (to determine the preventive activity) the treatment with the arylhydrazo-aldoxime, and by treating said plants with the fungicidal agent in parts far from the point of infection (to determine the immunizing activity).

The following examples are given for the purpose of illustrating the present invention in more detail, and are not intended to be limiting. Examples 1 and 2 illustrate the method of synthesizing the new compounds, the remaining examples concern the biological activity of some of the arylhydrazo-aldoximes within the scope of this invention.

EXAMPLE 1

M 6950

(a) An aqueous solution containing 44.5 g of 1-nitropropane and 20 g of NaOH was added, at 0° C. and in 30 minutes, to a hydro-alcoholic solution of diazonium salt prepared from 81 g of 3,4-dichloroaniline, 210 cc of concentrated HCl, 35 g of NaNO$_2$ and 225 g of trihydrated sodium acetate.

At the conclusion of the addition, the mass was stirred for 3 hours at 0° C., whereupon the resulting solid product was filtered. After washing with H$_2$O and drying, 125 g of 1-nitro-1-(3,4-dichlorophenyl-hydrazone)-propane were collected in the form of a yellow solid having a melting point of 137° C. with decomposition.

(b) 125 g of the 1-nitro-1-(3,4-dichlorophenylhydrazone)-propane were added to 400 cc of ethanol saturated at 0° C. with gaseous NH$_3$. Successively, anhydrous H$_2$S was made to bubble in the reaction mixture until evolvement of heat was no longer observed, and having ascertained that the inside temperature never exceeded 35° C. At the conclusion of the reaction, the solvent was removed at reduced pressure and the residual solid was washed with H$_2$O. There were obtained 75 g of β-(α-oximinopropyl)-3,4-dichlorophenylhydrazine in the form of a white solid having a melting point of 124° C. with decomposition.

EXAMPLE 2

M 6953

75 g of β-(α-oximino-propyl)-3,4-dichlorophenylhydrazine dissolved in a mixture of ethanol-ethyl ether were treated, at 5°–10° C., with anhydrous HCl up to an acid pH.

The solid which separated was filtered, so obtaining 75 g of β-(α-oximino-propyl)-3,4-dichlorophenylhydrazine hydrochloride in the form of white crystals having a melting point of 155° C. with decomposition.

EXAMPLE 3

Curative activity on vine mildew
(*Plasmopara viticola* (B et C) Berl. et de Toni)

The leaves of cv. Dolcetto vine, cultivated in pot in a conditioned ambient at 25° C. and 60% of relative humidity, were sprayed on their lower faces with an aqueous suspension of conides (200,000 conides/cc); after a residence time of 24 hours in a humidity-saturated ambient at 21° C., the plants were divided into three groups. The plants of each group were treated by spraying both faces of their leaves with the products being tested in a hydroacetone solution at 20% of acetone (vol./vol.) respectively after 1, 2 and 3 days from the infection.

At the conclusion of the incubation period (7 days), the seriousness of the infections was evaluated at sight according to indexes of an evaluation scale ranging from 100 (sound plant) to 0 (thoroughly infected plant).

| Product | Dose °/$_{oo}$ active product | Activity |
|---|---|---|
| 6425 | 1.5 | 75 |
| 6953 | 1.5 | 100 |
| 7007 | 1.5 | 42 |

| Product | Dose °/oo active product | Activity |
|---|---|---|
| 7008 | 1.5 | 100 |

EXAMPLE 4

Immunizing activity on vine mildew
(*Plasmopara viticola* (B et C) Berl et de Toni)

The leaves of cv. Dolcetto vine, cultivated in pot in a conditioned ambient, were sprayed on their upper faces with the product being tested in a hydroacetone solution at 20% of acetone (vol./vol.).

The plants were then kept in a conditioned ambient for 6 days; on the seventh day the lower faces of their leaves were sprayed with a suspension of conides of *Plasmopara viticola* (200,000 conides/cc); after a 24-hour residence time in a humidity-saturated ambient, the plants were brought again to a conditioned ambient.

At the conclusion of the incubation period (7 days), the seriousness of the infection was evaluated at sight according to indexes of an evaluation scale ranging from 100 (sound plant) to 0 (fully infected plant).

| Product | Dose °/oo active product | Activity |
|---|---|---|
| 6425 | 3 | 100 |
| 6953 | 3 | 100 |
| 7008 | 3 | 100 |

EXAMPLE 5

Curative activity on the beet Cercospora
(*Cercospora beticola* Sacc.)

The leaves of beet plants, cv. KWS polybeta, cultivated in a conditioned ambient, were sprayed on both faces with an aqueous suspension of conides of *Cercospora beticola* (200,000 conides/cc); after 48 hours said leaves were treated with the product being tested in a hydroacetone solution at 20% of acetone (vol./vol.) by spraying of both faces.

At the end of the incubation period (20 days), the seriousness of the infection was evaluated at sight according to indexes of an evaluation scale ranging from 100 (sound plant) to 0 (fully infected plant).

| Product | Dose °/oo active product | Activity |
|---|---|---|
| 6953 | 1 | 85 |
| 7007 | 1 | 46 |
| 7008 | 1 | 62 |
| 7010 | 1 | 100 |

EXAMPLE 6

Immunizing activity on beet Cercospora
(*Cercospora beticola* Sacc.)

The beet leaves, cv. KWS polybeta, cultivated in pot in a conditioned ambient, were sprayed on their upper faces with the product being tested in a hydroacetone solution at 20% of acetone (vol./vol.). The plants were then kept in a conditioned ambient for 6 days; on the 7th day the lower faces of the leaves were sprayed with a suspension of conides of *Cercospora beticola* (200,000 conides/cc). After a residence time of 48 hours in a humidity-saturated ambient, the plants were brought again into a conditioned ambient.

At the conclusion of the incubation period (20 days), the seriousness of the infection was evaluated at sight according to indexes of an evaluation scale ranging from 100 (sound plant) to 0 (fully infected plant).

| Product | Dose °/oo active product | Activity |
|---|---|---|
| 6953 | 1 | 72 |
| 7007 | 1 | 86 |
| 7008 | 1 | 84 |
| 7010 | 1 | 100 |

EXAMPLE 7

Curative activity on cucumber oidium
(*Sphaerotheca fuliginea* [Schlech] Salmon.)

The leaves of cucumber plants, cv. Marketer, cultivated in pot in a conditioned ambient, were sprayed on their upper faces with an aqueous suspension of conides of *Sphaerotheca fuliginea* (200,000 conides/cc); after 24 hours said leaves were treated with the product being tested in a hydroacetone solution at 20% of acetone (vol./vol.) by spraying of both faces.

At the conclusion of the incubation period (8 days), the seriousness of the infection was evaluated at sight according to indexes of an evaluation scale ranging from 100 (sound plant) to 0 (fully infected plant).

| Product | Dose °/oo active product | Activity |
|---|---|---|
| 6425 | 0.3 | 80 |
| 6881 | 0.3 | 80 |
| 6953 | 0.3 | 100 |
| 7007 | 0.3 | 100 |
| 7008 | 0.3 | 100 |
| 7010 | 0.3 | 87 |
| 7496 | 0.3 | 100 |

EXAMPLE 8

Immunizing activity on cucumber oidium (*Sphaerotheca fuliginea* [Schlech] Salmon.)

The leaves of cucumber plants, c.v. Marketer, cultivated in pot in a conditioned ambient, were sprayed on their lower faces with the product being tested in a hydroacetone solution at 20% of acetone (vol./vol.). The plants were then maintained in a conditioned ambient per 6 days; on the 7th day the upper faces of the leaves were sprayed with an aqueous suspension of conides of Sphaerotheca fuliginea (200.000 conides/cc.); then the plants were brought again into a conditioned ambient.

At the conclusion of the incubation period (8 days), the seriousness of the infection was evaluated at sight according to indexes of an evaluation scale ranging from 100 (sound plant) to 0 (fully infected plant).

| Product | Dose °/oo active product | Activity |
|---|---|---|
| 6953 | 0.1 | 100 |
| 7496 | 0.1 | 50 |
| 7008 | 0.1 | 74 |
| 7010 | 0.1 | 40 |

EXAMPLE 9

Curative activity on bean rust
(*Uromyces appendiculatus* (Pers.) Link)

The leaves of the bean Borlotto di Vigevano, cultivated in pot in a conditioned ambient, were sprayed on their lower faces with an aqueous suspension of spores of *Uromyces appendiculatus* (200,000 spores/cc); after a residence time of 24 hours in a humidity-saturated ambient, said leaves were treated with the product being tested in a hydroacetone solution at 20% of acetone (vol./vol.) by spraying both faces of the leaves.

At the conclusion of the incubation period (14 days), the seriousness of the infection was evaluated at sight according to indexes of an evaluation scale ranging from 100 (sound plant) to 0 (completely infected plant).

| Product | Dose °/oo active product | Activity |
|---------|--------------------------|----------|
| 6425 | 0.5 | 100 |
| 6881 | 0.5 | 100 |
| 7007 | 0.5 | 80 |
| 7496 | 0.5 | 100 |

EXAMPLE 10

Immunizing activity on bean rust
(*Uromyces appendiculatus* (Pers.) Link.)

The leaves of the bean cv. Borlotto di Vigevano, cultivated in pot in a conditioned ambient, were sprayed on their upper faces with the product being tested in a hydroacetone solution at 20% of acetone (vol./vol.). The plants were then maintained in a conditioned ambient for 6 days; on the seventh day the lower faces of the leaves were sprayed with a suspension of spores of *Uromyces appendiculatus* (200,000 spores/cc); after a residence time of 24 hours in a humidity-saturated ambient, the plants were brought again into a conditioned ambient.

At the conclusion of the incubation period (14 days), the seriousness of the infection was evaluated at sight, according to indexes of an evaluation scale ranging from 100 (sound plant) to 0 (fully infected plant).

| Product | Dose °/oo active product | Activity |
|---------|--------------------------|----------|
| 6425 | 1 | 100 |
| 7007 | 1 | 70 |
| 6881 | 1 | 28 |
| 7496 | 1 | 95 |

What we claim is:

1. The method of combatting fungi infections of useful plants, or of preventing such infections, which method consists of applying to the plants a fungicidally effective amount of arylhydrazo-aldoximes having the formula:

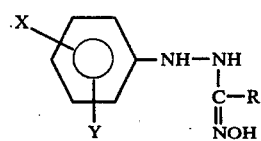

in which

X and Y are H, halogen, $C_1$-$C_5$ alkyls, —$CF_3$, —$OCH_3$ or $NO_2$; and

R is H, $C_1$-$C_5$ alkyl, phenyl or phenyl substituted with 1 or 2 halogen atoms;

tautomers of said arylhydrazo-aldoximes, organic salts of said arylhydrazo-aldoximes, or inorganic salts of said arylhydrazoaldoximes.

2. The method of claim 1, in which the fungicidally active arylhydrazo-aldoxime tautomer thereof, or organic or inorganic salt thereof, is applied to the plants to be treated in an amount of at least 0.1% by weight.

3. The method of claim 1, in which the fungus is *Plasmopara viticola* (B et C) Berl. et de Toni.

4. The method of claim 1, in which the fungus is *Cercospora beticola* Sacc.

5. The method of claim 1, in which the fungus is *Sphaerotheca fuligines* (Schlech) Salmon.

6. The method of claim 1, in which the fungus is *Uromyces appendiculatus* (Pers.) Link.

7. A formulation for combatting fungi infections of useful plants, or of preventing such infections, which formulation contain an inert carrier and, as active principle thereof, a fungicidally effective amount of arylhydrazo-aldoximes having the formula:

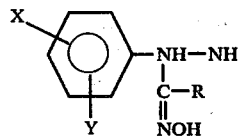

in which

X and Y are H, halogen, $C_1$-$C_5$ alkyls, —$CF_3$, —$OCH_3$ or $NO_2$; and

R is H, $C_1$-$C_5$ alkyl, phenyl, or phenyl substituted with one or two halogen atoms; tautomers of said arylhydrazo-aldoximes, organic salts of said arylhydrazo-aldoximes or inorganic salts of said arylhydrazo-aldoximes.

* * * * *